(12) United States Patent
Vodyanoy et al.

(10) Patent No.: US 7,106,503 B2
(45) Date of Patent: Sep. 12, 2006

(54) HIGH-RESOLUTION OPTICAL MICROSCOPE

(75) Inventors: Vitaly J. Vodyanoy, Auburn, AL (US); William Charles Neeley, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 11/068,223

(22) Filed: Feb. 28, 2005

(65) Prior Publication Data

US 2005/0168810 A1    Aug. 4, 2005

Related U.S. Application Data

(62) Division of application No. 10/674,783, filed on Sep. 30, 2003, now Pat. No. 6,865,013, which is a division of application No. 10/008,588, filed on Dec. 3, 2001, now Pat. No. 6,690,509.

(60) Provisional application No. 60/250,800, filed on Dec. 1, 2000.

(51) Int. Cl.
*G02B 21/00* (2006.01)

(52) U.S. Cl. ............... 359/368; 359/387; 359/327; 356/301

(58) Field of Classification Search ............... 359/368, 359/588, 385–390, 618–640, 370, 371, 327; 356/301; 422/73
See application file for complete search history.

(56) References Cited

U.S. PATENT DOCUMENTS

| | | | |
|---|---|---|---|
| 4,398,211 A | 8/1983 | Young | |
| 4,405,237 A | 9/1983 | Manuccia et al. | |
| 4,498,749 A | 2/1985 | Hoover | |
| 4,645,340 A | 2/1987 | Graham et al. | |
| 4,737,022 A | 4/1988 | Faltermeier et al. | |
| 4,762,413 A | 8/1988 | Namba et al. | |
| 4,766,083 A | 8/1988 | Miyashita et al. | |
| 4,852,985 A | 8/1989 | Fujihara et al. | |
| 4,887,892 A | 12/1989 | Bacus | |
| 4,988,630 A | 1/1991 | Chen et al. | |
| 4,999,495 A | 3/1991 | Miyata et al. | |
| 5,270,853 A | 12/1993 | Bashkansky et al. | |
| 5,291,012 A | 3/1994 | Shimzu et al. | |
| 5,418,797 A | 5/1995 | Bashkansky et al. | |
| 5,426,302 A | 6/1995 | Marchman et al. | |
| 5,434,901 A | 7/1995 | Nagai et al. | |

(Continued)

FOREIGN PATENT DOCUMENTS

CA    2437013    10/1998

(Continued)

OTHER PUBLICATIONS

Board of Regents, The Smithsonian Institution, "Rife's Microscope—The Smithsonian Report," Annual Report, 1944.

(Continued)

*Primary Examiner*—Mark A. Robinson
*Assistant Examiner*—Lee Fineman
(74) *Attorney, Agent, or Firm*—Gardner Groff Santos & Greenwald, PC

(57) ABSTRACT

A direct-view optical microscope system is provided which uses high-energy light from a phenomenon known as non-resonant Raman scattering to illuminate a living biological specimen. One embodiment of the system combines two discrete light sources to form a combined incident light source for the microscope. The system includes a method and apparatus for modulating the intensity of the scattered light when two light waves are combined to produce the incident light. By varying the frequency of the two source light waves, the intensity of the combined Raman-scattered light can be modulated to achieve finer resolution.

7 Claims, 13 Drawing Sheets

U.S. PATENT DOCUMENTS

| | | |
|---|---|---|
| 5,508,517 A | 4/1996 | Onuki et al. |
| 5,528,368 A | 6/1996 | Lewis et al. |
| 5,563,412 A | 10/1996 | Zandbergen et al. |
| 5,684,588 A | 11/1997 | Khoury et al. |
| 5,770,416 A | 6/1998 | Lihme et al. |
| 5,808,790 A | 9/1998 | Otaki |
| 5,841,577 A | 11/1998 | Wachman et al. |
| 5,859,713 A | 1/1999 | Khoury et al. |
| 5,870,188 A | 2/1999 | Ozaki et al. |
| 5,946,128 A | 8/1999 | Paek |
| 5,952,657 A | 9/1999 | Alexander et al. |
| 6,006,140 A | 12/1999 | Carter |
| 6,014,245 A | 1/2000 | Xu et al. |
| 6,061,176 A | 5/2000 | Shih |
| 6,064,060 A | 5/2000 | Konada |
| 6,108,081 A | 8/2000 | Holtom et al. |
| 6,127,681 A | 10/2000 | Sato et al. |
| 6,130,776 A | 10/2000 | Takaoka |
| 6,215,587 B1 | 4/2001 | Alfano et al. |
| 6,226,118 B1 | 5/2001 | Koyama et al. |
| 6,271,963 B1 | 8/2001 | Freifeld |
| 6,274,871 B1 | 8/2001 | Dukor et al. |
| 6,330,058 B1 | 12/2001 | Garcia-Rubio et al. |
| 6,455,838 B1 | 9/2002 | Schaffer et al. |
| 6,542,251 B1 | 4/2003 | Mueller-Rentz |
| 6,590,703 B1 | 7/2003 | Park et al. |
| 6,608,670 B1 | 8/2003 | Nottke et al. |
| 6,690,509 B1 | 2/2004 | Vodyanoy et al. |

FOREIGN PATENT DOCUMENTS

| | | |
|---|---|---|
| CA | 2365093 | 1/2000 |
| CA | 2441726 | 8/2000 |
| EP | 1 324 096 A2 | 2/2003 |
| EP | 1 097 396 B1 | 3/2003 |
| GB | 2195467 A1 | 4/1998 |
| JP | 09-297266 | 11/1997 |
| WO | WO 98/45744 A1 | 10/1998 |
| WO | WO 02/016485 A2 | 8/2002 |
| WO | WO 02/061485 A3 | 8/2002 |

OTHER PUBLICATIONS

Gage, Simon H., "Special Oil-Immersion Objectives for Dark-Field Microscopy," SCIENCE, New Series, vol. 54, No. 1406, pp. 567-569, Dec. 9, 1921.

Kopac, M.J., "Darkfield Micromanipulation with an Ultrapaque Illuminator," SCIENCE, New Series, vol. 82, No. 2116, p. 70, Jul. 19, 1935.

International Searching Authority, International Search Report and Written Opinion; mailed Dec. 11, 2004; regarding International Application No. PCT/US2004/017948 (European Patent Office).

MacNeal, Ward, J., et al., "A Culture Slide for Dark-Field Microscopy," SCIENCE, New Series, vol. 88, No. 2293, p. 554 Dec. 9, 1983.

Matsunaga, Sachihiro, et al., "Clear Visualization of the Products of Non-radioactive in situ Hybridization in Plant Tissue by Simple Dark-Field Microscopy," MICRON, vol. 28, No. 3, pp. 185-187, 1997.

Raman, C.V., et al, "A New Type of Secondary Radiation," vol. 121, pp. 501-502, Mar. 31, 1928.

Rosenow, Edward C., "Discussion: Observations with the Rife Microscope of Filter-Passing Forms of Microorganisms," Annual Report of the Board of Regents, The Smithsonian Institution, 1944.

Seidel, M.D., R.E., et al., "The New Microscopes," Journal of the Franklin Institute, vol. 237, No. 2, pp. 103-130, 1994.

Senatorov, Vladimir V., "Dark-Field Microscopy Visualization of Un-stained Axonal Pathways Using Oil of Wintergreen," Journal of Neuroscience Methods, vol. 113, pp. 59-62, 2002.

Totzeck, M., et al, "Phase-Shifting Polarization Interferometry for Microstructure Linewidth Measurement," Optics Letters; Optical Society of America, vol. 24, No. 5, pp. 294-296, Mar. 1, 1999.

Wachman, E., et al, "Imaging acousto-optic tunable filter with 0.35-micometer spatial resolution," Applied Optics; Optical Society of America, vol. 35, No. 5, pp. 5220-5226, Sep. 1996.

Witlin, Bernard, "Darkfield Illuminators in Microscopy," SCIENCE, New Series, vol. 102, No. 2637, pp. 41-42, Jul. 13, 1945.

HIGH-RESOLUTION OPTICAL MICROSCOPE

RELATED APPLICATIONS

This application is a divisional of U.S. patent application Ser. No. 10/674,783 filed Sep. 30, 2003 now U.S. Pat. No. 6,865,013; which in turn is a divisional of U.S. patent application Ser. No. 10/008,588 filed Dec. 3, 2001, now U.S. Pat. No. 6,690,509; which in turn claims the benefit and priority of U.S. Provisional Application Ser. No. 60/250,800, filed Dec. 1, 2000. Said applications are hereby incorporated herein by reference in their entireties for all purposes.

TECHNICAL FIELD

The present invention relates generally to the field of direct-view optical microscopes and, more particularly, to a method and apparatus for using high-energy light from a phenomenon known as non-resonant Raman scattering to illuminate a living biological specimen.

BACKGROUND OF THE INVENTION

Since their invention in the late 1500s, light microscopes have enhanced our knowledge of basic biology, biomedical research, medical diagnostics, and materials science. Although the science of microscopy has advanced to include a variety of techniques to enhance resolution, the fine-resolution observation of living biological specimens has remained elusive.

Continuing advances in microbiology require a closer and closer study of biochemical events that occur on a cellular and intracellular level. The challenge in microscopy today is not only the enhancement of finer and finer resolution, but also the development of techniques for observing biochemical events in real time, as they happen, without destroying the biological specimen in the process.

Resolution is the ability of a microscope to distinguish between two objects that are very close together. A microscope with a resolution of 1,000 Å (1,000 Angstroms; equal to 100 nanometers or $100 \times 10^{-9}$ meters), for example, can make objects as close together as 100 nanometers independently visible. Objects and features smaller than 100 nanometers cannot be resolved (i.e., distinguished) by this microscope. Below is a list of the resolution or practical resolving power of several types of microscopes currently available:

| | |
|---|---|
| 2,000 Å | Visible Light Microscope |
| 1,000 Å | Ultraviolet Microscope |
| 150 to 300 Å | Scanning Electron Microscope |
| 2.0 to 4.0 Å | Transmission Electron Microscope |

Although electron microscopes offer very fine resolution, the specimen must be prepared by high-vacuum dehydration and is subjected to intense heat by the electron beam, making observation of living specimens impossible. The dehydration process also alters the specimen, leaving artifacts and cell damage that were not present in nature. Also, In order to view the steps in a biological process, dozens of specimens must be viewed at various stages in order to capture each desired step in the process. The selected specimens must then be prepared. Specimen preparation can take up to two hours each.

The high cost of an electron microscope represents another barrier to its use in the life sciences. Electron microscopes are large and often require an entire room. The operation and adjustment of an electron microscope requires highly-skilled technicians, introducing yet another cost of maintaining and staffing an electron microscopy facility.

The ultraviolet microscope offers finer resolution and better magnification than an ordinary light microscope, but it has serious disadvantages for the study of living specimens. Ultraviolet light damages or kills many kinds of living biological specimens, making observation impossible.

When ultraviolet light strikes a specimen, it excites fluorescence within the molecules of the specimen so that the specimen itself emits a fluorescent light. If the specimen does not produce fluorescence naturally, it must be stained with a fluorescent dye. Many fluorescent dyes bind strongly to elements such as enzymes within living cells, changing their qualities and significantly altering the cellular biochemistry. Other dyes produce too much fluorescence or absorb too much of the ultraviolet light to be useful.

Like electron microscopes, the operation of an ultraviolet microscope requires a great deal of skill. Because ultraviolet light damages the human eye, the image can only be observed by ultraviolet video cameras or specially-equipped still cameras. Also, the quartz optics required for ultraviolet microscopes are much more expensive than the glass components used in visible light microscopes.

The electron and ultraviolet microscopes available today do no offer a technique for observing living, unaltered biological specimens in real time.

The Nature of Light

Light is sometimes referred to as a type of electromagnetic radiation because a light wave consists of energy in the form of both electric and magnetic fields. In addition to the light we can see, the electromagnetic spectrum includes radio waves, microwaves, and infrared light at frequencies lower than visible light. At the upper end of the spectrum, ultraviolet radiation, x-rays, and gamma rays travel at frequencies faster than visible light.

Wavelength is the distance between any two corresponding points on successive light waves. Wavelength is measured in units of distance, usually billionths of a meter. The human eye can see wavelengths between 400 and 700 billionths of a meter.

Frequency is the number of waves that pass a point in space during any time interval, usually one second. Frequency is measured in units of waves per second, or Hertz (Hz). The frequency of visible light is referred to as color. For example, light traveling at 430 trillion Hz is seen as the color red.

The wavelength of light is related to the frequency by this simple equation (Equation One), $$f = \frac{c}{L},$$

where c is the speed of light in a vacuum (299,792,458 meters per second), f is the frequency in Hz, and L is the wavelength in meters.

Microscope Resolution

The resolution or resolving power of a light microscope can be calculated using Abbe's Formula, $$D = \frac{L}{2(NA)},$$

where D is the resolving power of a microscope in meters, L is the wavelength in meters of the light source, and NA is the numerical aperture of the microscope. The numerical aperture, generally, indicates the angle at which light strikes the specimen being viewed.

Light Scattering

When a light wave passes through a specimen, most of the light continues in its original direction, but a small fraction of the light is scattered in other directions. The light used to illuminate the specimen is called the incident light. The scattering of incident light through various specimens was studied by Lord John William Strutt, the third Baron Rayleigh (Lord Rayleigh) in the late 1800s and later by Albert Einstein and others.

Lord Rayleigh observed that a fraction of the scattered light emerges at the same wavelength as the incident light. Because of his observation, light that is scattered at the same wavelength as the incident light is a phenomenon called Rayleigh scattering (also called resonant scattering or elastic light scattering).

In 1922, Arthur H. Compton observed that some of the scattered light has a different wavelength from the incident light. Compton discovered that, when light passes through a specimen, some of the light scatters off the electrons of the specimen molecules, producing scattered light in the X-ray region of the spectrum.

Raman Scattering

In 1928, Professor Chandrasekhara V. Raman and Professor K. S. Krishnan discovered that the scattered light observed by Compton was caused by vibrations within the molecules of the specimen. Because of his discovery, light that is scattered due to vibrations within the molecules of a specimen is a phenomenon called Raman scattering (also called non-resonant or inelastic light scattering). In 1930, Raman received the Nobel Prize in Physics for his discovery.

When a specimen is bombarded with incident light, energy is exchanged between the light and the molecules of the specimen. The molecules vibrate, producing the phenomenon known as Raman scattering. The molecular vibrations cause the specimen itself to emit scattered light, some of which scatters at a higher frequency (f+Δf) than the incident light frequency (f), and some of which scatters at a lower frequency (f−Δf). The Δf represents the change in frequency (sometimes called the frequency shift) produced by Raman scattering.

In summary, when incident light strikes a specimen, the scattered light includes Rayleigh-scattered light at the same frequency (f) as the incident light, higher frequency (f+Δf) Raman-scattered light, and lower-frequency (f−Δf) Raman-scattered light.

Intensity Depends on the Specimen

Because Raman-scattered light is produced by molecular vibrations within the specimen, the intensity of the Raman-scattered light varies depending upon the type of specimen being viewed. For example, a specimen of blood cells may produce high-intensity Raman-scattered light, while a specimen of skin cells may produce very low-intensity Raman-scattered light.

Raman scattering is used in a variety of spectroscopy systems to study the interaction between a sample and certain types of incident light. The fact that Raman scattering varies depending on the specimen, however, has limited its direct use in the field of microscopy. Although the phenomenon of light scattering is present whenever light strikes a specimen, none of the microscopy systems available today are configured to fully harness the resolving power of Raman scattering.

Thus, there is a need in the art for a microscopy system that takes full advantage of the Raman scattering phenomenon as a source of illuminating a specimen.

There is a related need for a system for relaying and capturing the images produced by such a microscope. There is yet another related need in the art for producing and adapting the types of incident light best suited for provoking Raman scattering in a biological specimen.

There is also a need in the art for a direct-view, optical microscope with a higher resolution and magnification than is currently available.

There is further a need for an optical microscope that provides a real-time image of living biological materials, including cells and intracellular structures. There is a related need for a microscope that permits observation by the human eye and recording by readily-available photomicrographic and video equipment.

There is also a need to provide a system and method for viewing living biological specimens in their natural state, without interference from the artifacts of specimen preparation, without destroying or altering sensitive biochemical characteristics, and without killing the specimen.

There is still further a need for a high-resolution microscope that is less expensive, easy to operate, requires little or no specimen preparation, and is relatively portable and small enough for use in the field.

SUMMARY OF THE INVENTION

The above and other needs are met by the present invention which, stated generally, provides a direct-view optical microscope system that uses high-energy light from a phenomenon known as non-resonant Raman scattering to illuminate a living biological specimen.

In one aspect of the present invention, a microscope system for observing a specimen includes an optical microscope, a light source, a darkfield condenser to focus the light on the specimen, and a compound relay lens connected to the eyepiece of the microscope. The light source is ultraviolet in one embodiment. The system may also include an adapter positioned between the light source and the microscope to align the light. The system may also include a camera and a computer.

The compound relay lens of the present invention includes two relay lenses connected together to provide higher magnification than a single relay lens alone.

In another aspect, the invention provides of method of provoking enough light scattering to illuminate a specimen in an optical microscope system. The method includes illuminating a lamp that emits ultraviolet light, focusing the ultraviolet light upon the specimen using a darkfield condenser, and then magnifying the image of said specimen using said compound relay lens. The method may further include adapting the ultraviolet light for use in the microscope by positioning an adapter between the lamp and the darkfield condenser.

The method may also include the double oil immersion technique, which includes the steps of placing a drop of oil on the underside center of the slide on which the specimen rests, positioning the slide on the center of the darkfield condenser, placing a drop of oil on the top center of the cover glass, and then raising the darkfield condenser until the oil on the top of said cover glass contacts the objective lens.

In another aspect of the present invention, a microscope system is provided for illuminating and observing a specimen with scattered light from a combined light source. This system includes an optical microscope, a first light wave traveling at a first frequency, a second light wave traveling at a second frequency, an optical combiner to combine the two light waves into one, and a darkfield condenser. The combined light wave includes an additive light wave traveling at an additive frequency and a subtractive light wave traveling at a subtractive frequency. The darkfield condenser focuses the combined light upon the specimen such that the additive and subtractive light waves provoke scattered light.

In one embodiment of the two-light system, the first light wave is produced by a first light filtering system that includes a first light source emitting an unrefined light wave, a first filter, and a first filter controller. The filter controller sends a first control signal to the first filter based upon the desired frequency. The first filter then refines the unrefined light wave into a first light wave traveling at a first frequency. The second light wave is produced by a similar second light filtering system.

The two-light system may also include a compound relay lens, a camera, and a computer. In one embodiment, the two-light system includes an optical combiner. According to the present invention, the optical combiner includes a chamber, a casing enclosing said chamber and including several input ports and an output port, and a prism assembly configured to combine two incoming light waves into a single, combined light wave and project it through the output port.

In another aspect of the two-light system of the present invention, a system for producing the first and second light waves includes a dual-channel filter and a dual-frequency filter controller. The filter controller is configured to send a primary and a secondary control signal to the filter. The dual-channel filter broadcasts the first light wave on a first channel in response to the primary control signal and, in an alternating fashion, broadcasts the second light wave on a second channel in response to the secondary control signal.

In one embodiment, each control signal produces a corresponding acoustic wave inside the dual-channel filter. The first acoustic wave interacting with the unrefined light wave produces the first light wave, and the second acoustic wave interacting with the unrefined light wave produces the second light wave.

In another embodiment, the dual-frequency filter controller includes a primary radio frequency synthesizer, a secondary radio frequency synthesizer, and a driver connecting both synthesizers to the dual-channel filter. Each radio frequency synthesizer is configured to synthesize and send a control signal via the driver to the dual-channel filter.

In another aspect of the present invention, an optical combiner for combining two light waves to produce a single combined light wave includes a chamber, a casing enclosing said chamber and including several input ports and an output port, and a prism assembly configured to combine two incoming light waves into a single, combined light wave and project it through the output port.

In one embodiment, the optical combiner also includes a beam expander connected to each input port designated for light waves emitted by a laser. The beam expander focuses and collimates each incoming laser beam before it reaches the prism.

In an alternative embodiment, the optical combiner is capable of combining a laser light wave and an ultraviolet light wave. The optical combiner is also capable of receiving a single light wave entering through any one of the input ports, and projecting the single light wave through the output port.

In another aspect of the present invention, a method of modulating the combinatory phenomenon to illuminate and view a specimen in an optical microscope system with a combined light includes the steps of filtering a first unrefined light wave to produce a first light wave traveling at a first frequency, filtering a second unrefined light wave to produce a second light wave traveling at a second frequency, combining the light waves into a combined light wave, condensing the combined light, and focusing the combined light upon the specimen. The combined light wave includes an additive light wave traveling at an additive frequency and a subtractive light wave traveling at a subtractive frequency.

The method may also include placing a lower oil drop on the underside center of the slide, positioning the slide on the center of the darkfield condenser, placing an upper oil drop on the top center of the cover glass, and raising the darkfield condenser until the upper oil drop contacts the objective lens of the microscope.

Thus, it is an object of the present invention to provide a microscopy system that takes full advantage of the Raman light scattering phenomenon as a source of illuminating a specimen. It is a related object of the present invention to effectively relay the images captured by such a microscope system for maximum magnification.

It is also an object of the present invention to produce the types of incident light best suited for provoking light scattering in a biological specimen.

It is a further object of the present invention to provide an optical microscope that provides a real-time image of living biological materials, including cells and intracellular structures, that permits direct observation by the human eye, and that facilitates recording by readily-available photomicrographic and video equipment.

It is another object of the present invention to provide a system and method for viewing living biological specimens in their natural state, without interference from the artifacts of specimen preparation, without destroying or altering sensitive biochemical characteristics, and without killing the specimen.

It is also an object of the present invention to provide a fine-resolution, high-magnification microscope that is less expensive, easier to operate, more portable, and less labor-intensive in terms of specimen preparation than ultraviolet, electron, or other types of microscopes.

These and other objects are accomplished by the apparatus, method, and system disclosed and will become apparent from the following detailed description of one preferred embodiment in conjunction with the accompanying drawings.

DETAILED DESCRIPTION

Figure 1:
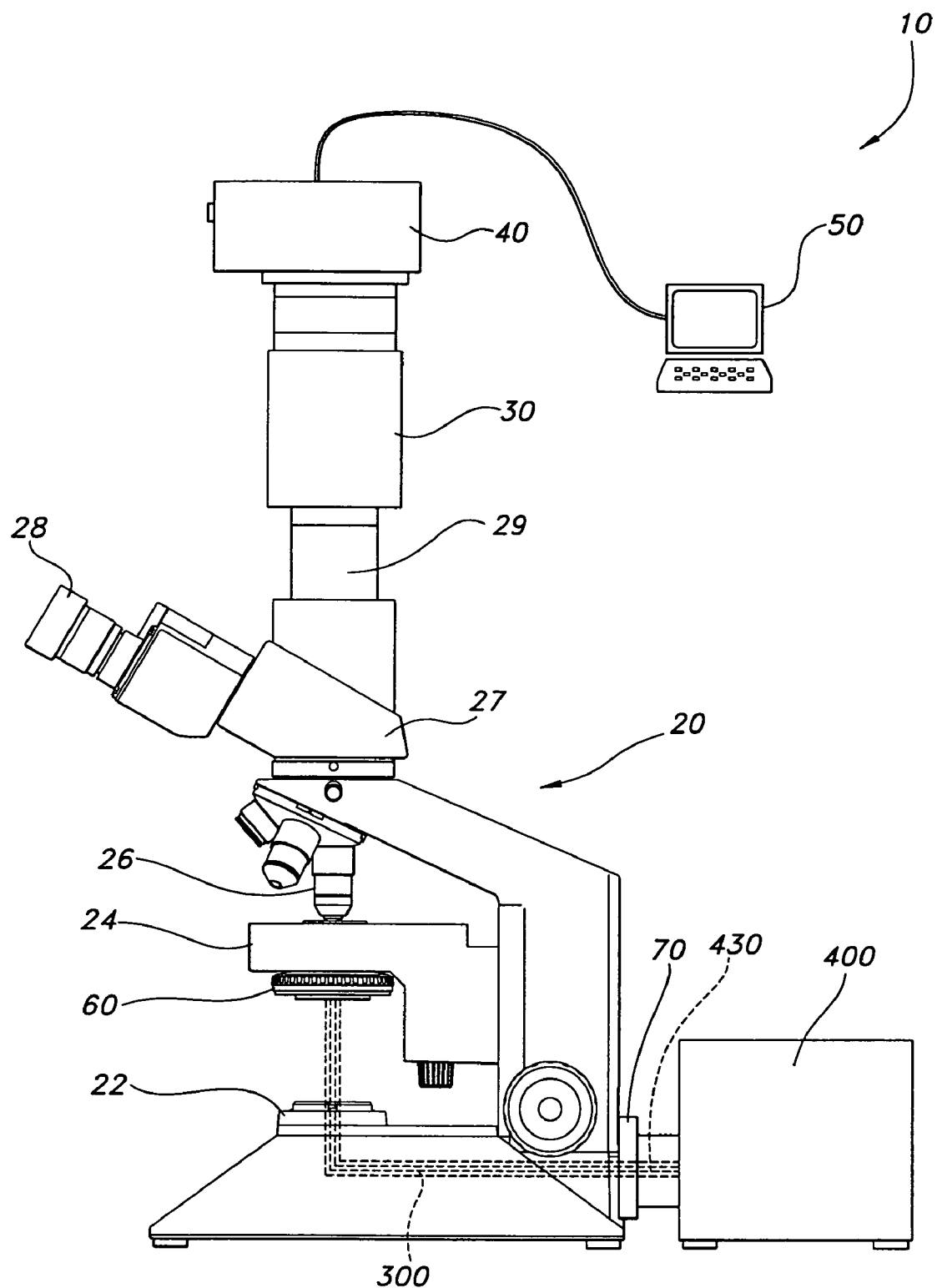
FIG. 1 is a diagrammatic side view of a microscope system according to an embodiment of the present invention.
Figure 11:
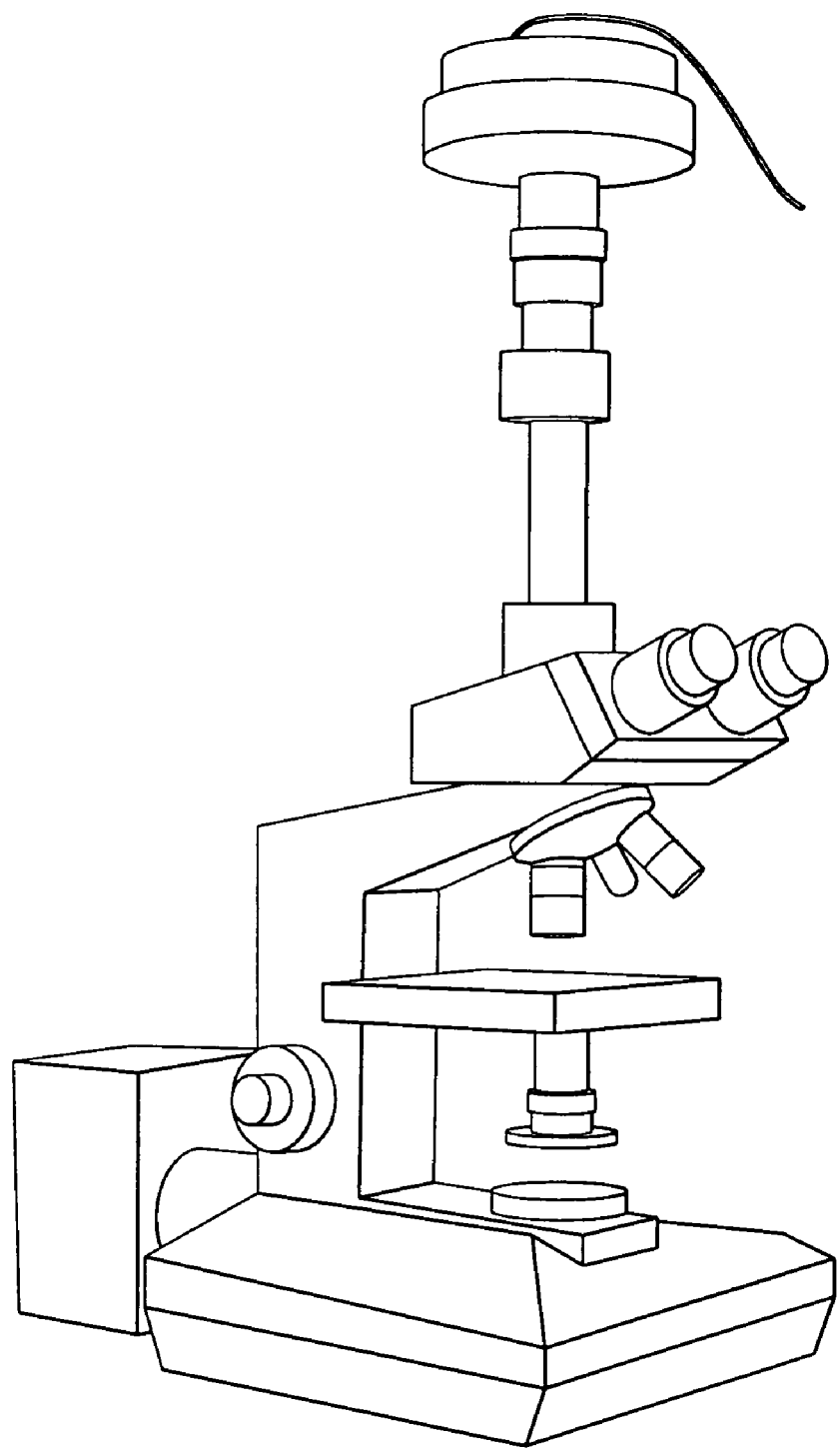
FIG. 11 is a perspective view of one embodiment of the microscope system according to the present invention.

Reference is now made to the drawing figures, in which like numerals refer to like elements throughout the several views. FIG. 1 shows one embodiment of an optical microscope system 10 according to the present invention. (FIG. 11 is a perspective view of one embodiment of the system 10). The system 10 shown in FIG. 1 includes a first light source 400, an adapter 70, a darkfield condenser 60, a direct-view optical microscope 20, a compound relay lens 30, a camera 40, and a computer 50. The first light source 400 emits a first light 430 which is called the incident light 300 once it enters the microscope 20.

A direct-view optical microscope 20 generally includes a base, a field diaphragm 22, a field condenser such as the darkfield condenser 60 shown, a stage 24 upon which a specimen may be placed, at least one objective lens 26, and at least one eyepiece for viewing or otherwise receiving the image captured by the objective lens 26. The term eyepiece includes a broad range of viewing devices beyond those which involve or are intended for the human eye. Light enters the objective lens 26 and travels into the trinocular head 27, which comprises an ocular eyepiece pair 28 for viewing with the eye and an upwardly-directed projection eyepiece 29.

The Compound Relay Lens

In one aspect of the inventive system 10 of the present invention, a compound relay lens 30 is added to the microscope 20 to magnify the image before it enters the camera 40, as shown in FIG. 1. A computer 50 receives the image.

Figure 2:
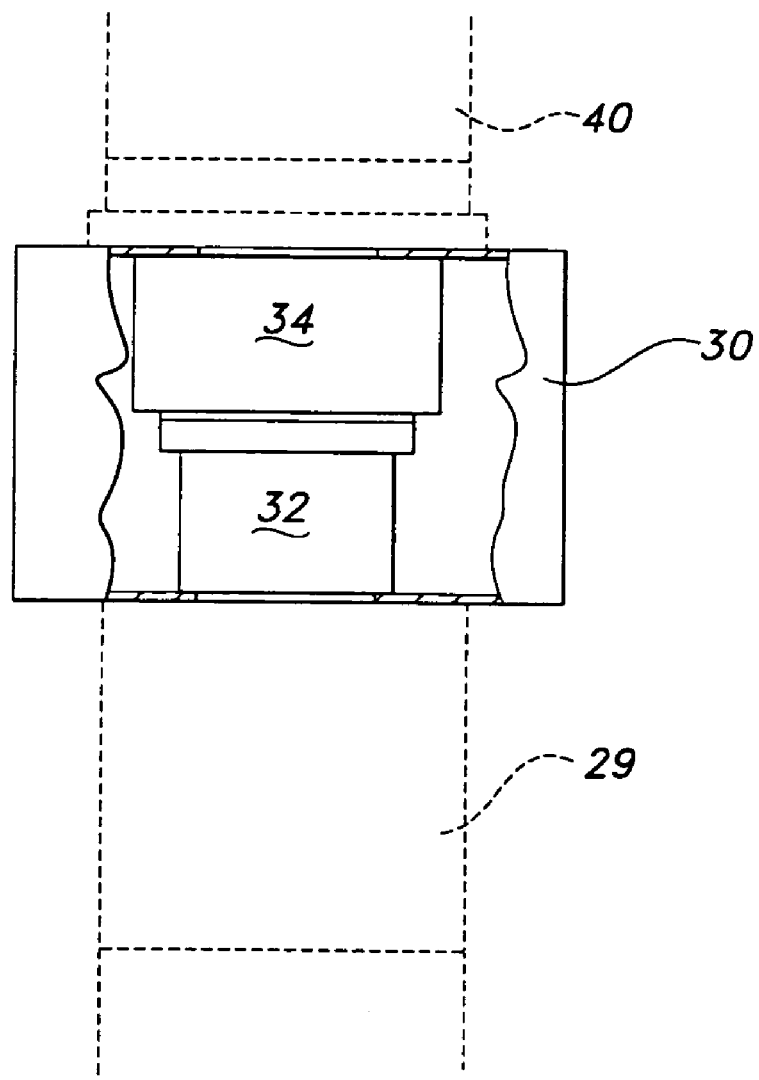
FIG. 2 is a diagrammatic side view of a compound relay lens according to an embodiment of the present invention.

A closer, schematic view of the compound relay lens 30 is shown in FIG. 2. The compound relay lens 30 generally includes a first relay lens 32 and a second relay lens 34. In one embodiment, the first relay lens 32 is a commercially-available objective lens having a cylindrical body and a C-type mount. The second relay lens 34 is a commercially-available relay lens. In a preferred embodiment, the first relay lens 32 has a numerical aperture of 0.65 and a magnification power of 40×, such as the Olympus model A40× objective lens. The second relay lens 34 has a magnification power of 10×, such as the Edmund model L37-820 relay lens. It should be understood that the compound relay lens 30 of the present invention contemplates the use of other types of lenses in combination with one another to produce an increased magnification of the image as it exits any of the eyepieces of the microscope 20. The combination of these lenses 32, 34 provides greater magnification than either lens would provide alone.

The Light Illuminating the Specimen

In the system 10 as shown in FIG. 1, a first light source 400 is used. In one embodiment, the first light source 400 is an ultraviolet light source 100, which emits a first light 430 having a frequency in the ultraviolet range of the electromagnetic spectrum (see FIG. 6). As depicted in FIG. 1, the first light 430 is called the incident light 300 once it enters the microscope 20.

When an ultraviolet light source 100 is used, the system 10 includes an adapter 70 which acts as an interface between the light source 100 and the visible-light optical microscope 20. The adapter 70 may include an enclosure such as a cylinder, with polished interior walls, and is configured to align the ultraviolet light source 100 with the entrance port of the microscope 20.

Figure 3:
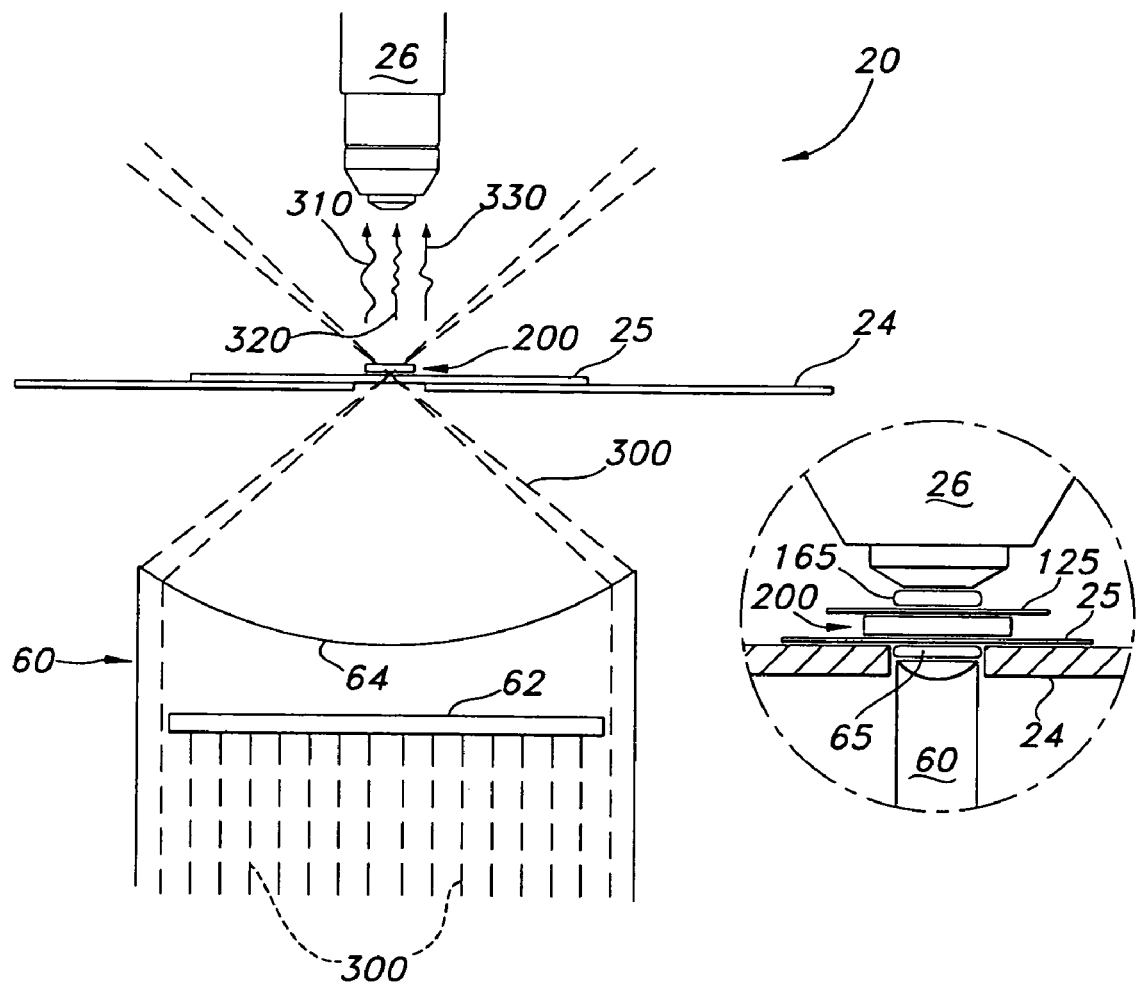
FIG. 3 is a detailed view of the incident light as it passes through a darkfield condenser, strikes a specimen, and enters an optical microscope, according to an embodiment of the present invention.

FIG. 3 provides a closer view of the stage 24 of the microscope 20, where the specimen 200 sits upon a slide 25. The ultraviolet first light 430 (now referred to as the incident light 300) enters the darkfield condenser 60 of the microscope 20. Each darkfield condenser 60 has a numerical aperture value NA, which indicates the angle at which light exits the condenser 60. A Naessens Darkfield Condenser having a numerical aperture NA of 1.41 produces excellent results, although other darkfield condensers may be used.

The darkfield condenser 60 generally includes an annular stop 62 and a condenser lens 64. In general, a darkfield condenser 60 directs the incident light 300 toward the specimen 200 at an angle that prevents most of the incident light 300 from entering the objective lens 26 of the microscope 20. The annular stop 62 is shaped like a disc and centrally mounted. Understanding the flow of light actually occurs in three dimensions, a hollow cylinder of light passes around the edges of the annular stop 62 and strikes the condenser lens 64, which bends the light toward the specimen 200 at an angle indicated by the numerical aperture NA. The incident light 300 exiting the condenser lens 64 is shaped like a hollow cone. By centering and adjusting the vertical position of the condenser 60, the cone of light can be positioned and focused such that its vertex strikes the specimen 200.

Scattered light is produced when the darkfield condenser 60 focuses the incident light 300 directly on the specimen 200. When the incident light 300 strikes the specimen 200, most of the light passes through and continues in its original direction, but a small fraction of the light is scattered in other directions. It is primarily the scattered light that enters the objective lens 26 of the microscope 20.

The scattered light, as shown in FIG. 3, includes a Rayleigh component 310, a high-frequency Raman component 320, and a low-frequency Raman component 330. The Rayleigh-scattered light 310 is emitted at the same frequency (f) as the incident light 300. The high-frequency Raman-scattered light 320 is emitted at a higher frequency (f+Δf). The lower-frequency Raman-scattered light 330 is emitted at a lower frequency (f−Δf).

The microscope system 10 shown in FIG. 1 is designed to take advantage of the high-energy light produced by Raman scattering 320 and use it to illuminate the specimen 200. It should be understood that types of light other than ultraviolet may be used in the system 10 of the present invention to excite Raman scattering to illuminate a specimen 200.

The Method

The method of using the microscope system 10 of the present invention produces sufficient scattered light 310, 320, 330 to illuminate a living biological specimen. An ultraviolet light enters the microscope 20 through an adapter 70 and is focused directly upon the specimen 200 by a darkfield condenser 60. The resulting image is magnified by a compound relay lens 30 and transmitted to a camera 40 and a computer 50, where the image may be further refined.

One method of using the system 10 includes the general steps of illuminating an ultraviolet light source 100 such as a mercury lamp, adapting the ultraviolet light for use in a visible-light microscope 20, and focusing the incident light 300 using a darkfield condenser 60 to provoke Raman-type light scattering to illuminate a living biological specimen 200. The method further includes magnifying the image using a compound relay lens 30 positioned between the microscope 20 and the camera 40.

In a preferred embodiment, the method of focusing the incident light 300 with the darkfield condenser 60 further includes a technique known as double oil immersion to enhance performance. A low-viscosity, low-fluorescence immersion oil is preferable. Preferably, a very thin cover glass 125 is positioned on top of the specimen 200, such that the specimen is sandwiched between the slide 25 and the cover glass 125.

The double oil immersion technique includes placing a drop of oil on the underside of the slide 25 and a drop of oil on the center of the cover glass 125. When the slide 25 is placed on the microscope stage 24, the oil on the underside will make immediate optical contact with the condenser 60. When the stage 24 is carefully raised until the oil on the top of cover glass 125 makes contact with the objective lens 26, all optical contacts will occur simultaneously and the specimen 200 will be illuminated.

In this position, as shown in the inset portion of FIG. 3, only the width of the lower oil drop 65 separates the condenser 60 from the slide 25 as it rests upon the stage 24 of the microscope 20. On the upper side, only the width of the upper oil drop 165 separates the cover glass 125 over the specimen 200 from the objective lens 26.

The Energy of Scattered Light

Figure 6:
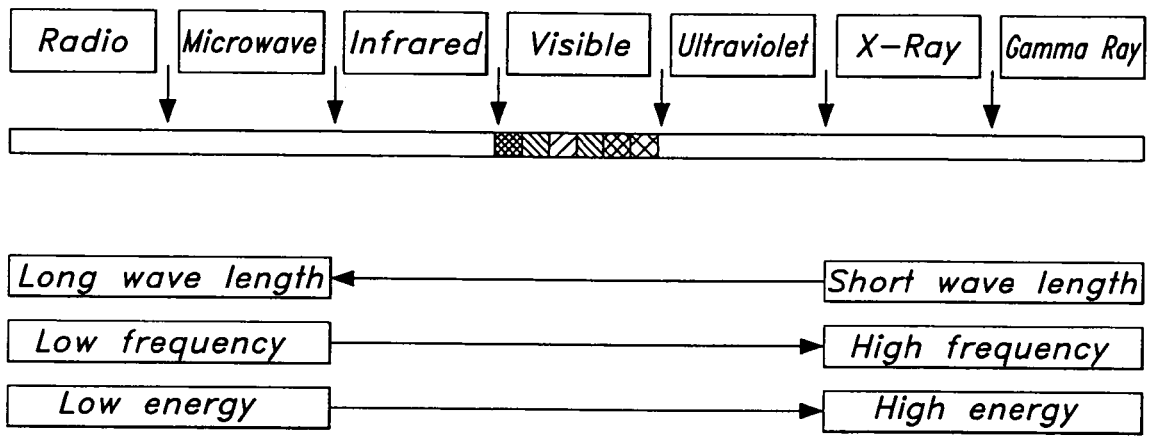
FIG. 6 is a graphical representation of the electromagnetic spectrum.

The higher frequency (f+Δf) Raman-scattered light waves 320 possess more energy than the incident light 300. Referring briefly to FIG. 6, the electromagnetic spectrum, it can be appreciated that higher-frequency, shorter-wavelength light waves possess higher energy. Because higher-energy light waves generally improve the resolution D of a microscope system 10, it is desirable to provoke a high amount of high-energy Raman-scattered light 320.

The intensity of Raman-scattered light 320, however, is about one-thousandth the intensity of Rayleigh-scattered light 310. Accordingly, it takes a very powerful (high energy and high frequency) light source to produce enough Raman-scattered light 320 to illuminate a specimen. Unfortunately, using a powerful light source also increases the amount of Rayleigh-scattered light 310, which can overpower and interfere with the Raman-scattered light 320.

Combining Two Light Sources

Figure 4:
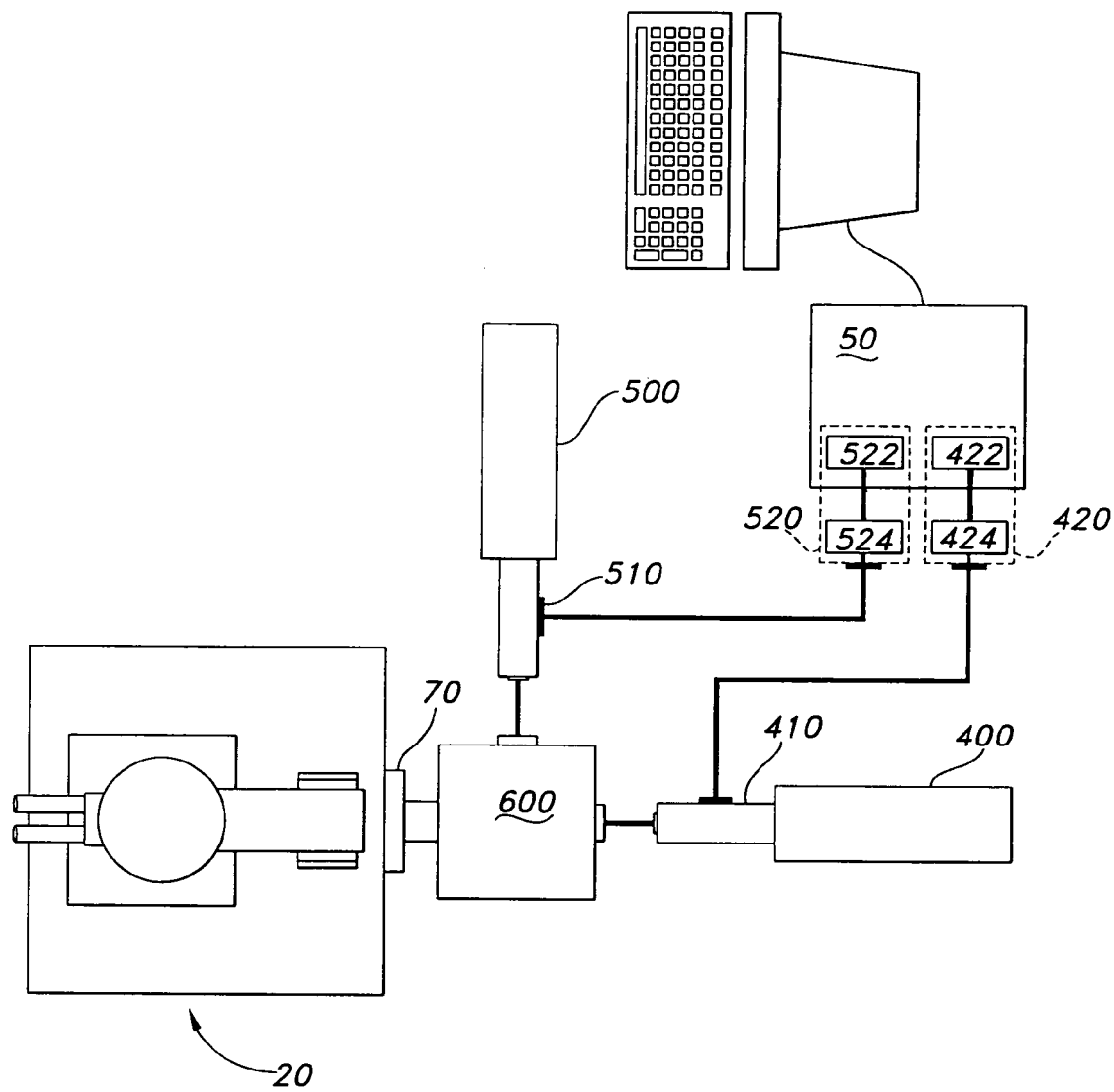
FIG. 4 is an overhead schematic view of a microscope system according to an embodiment of the present invention.

In another embodiment of the system 10 of the present invention, a method and apparatus is provided for maximizing Raman-type scattering while minimizing the interfering effects of Rayleigh-type scattering. In this embodiment, two light sources are combined, as shown in FIG. 4, to produce a combinatory phenomenon. The frequency of each light source can be adjusted to maximize the intensity of the Raman-scattered light 320 produced by the particular specimen 200 being viewed.

For example, although a specimen 200 of skin cells may produce a limited amount of Raman-scattered light 320 when illuminated by a single ultraviolet light source 100, using two adjustable light sources 400, 500 can increase the amount and intensity of Raman-scattered light 320 produced and, thus, increase the resolution D of the microscope system 10.

Referring to FIG. 4, a schematic view of this embodiment of the system 10 is depicted. The microscope system 10 includes a first light source 400, a second light source 500, an optical combiner 600, an adapter 70, and a direct-view optical microscope 20.

The first light source 400 is filtered by a first acousto-optic tunable filter 410 which is controlled by a first filter controller 420, which may be housed in a computer 50. Similarly, the second light source 500 is filtered by a second acousto-optic tunable filter 510 which is controlled by a second filter controller 520, which may be housed in a computer 50.

In one configuration, both the first and second light sources 400, 500 are lasers. The light emitted by a laser is well-suited to being filtered to a single frequency, and also well-suited for transmission using fiber optic cable. The laser may be an Argon-ion or Krypton-ion laser such as are available from Omnichrome Corporation, although other types of laser sources may be used.

The Acousto-Optic Tunable Filter (AOTF)

Figure 5:
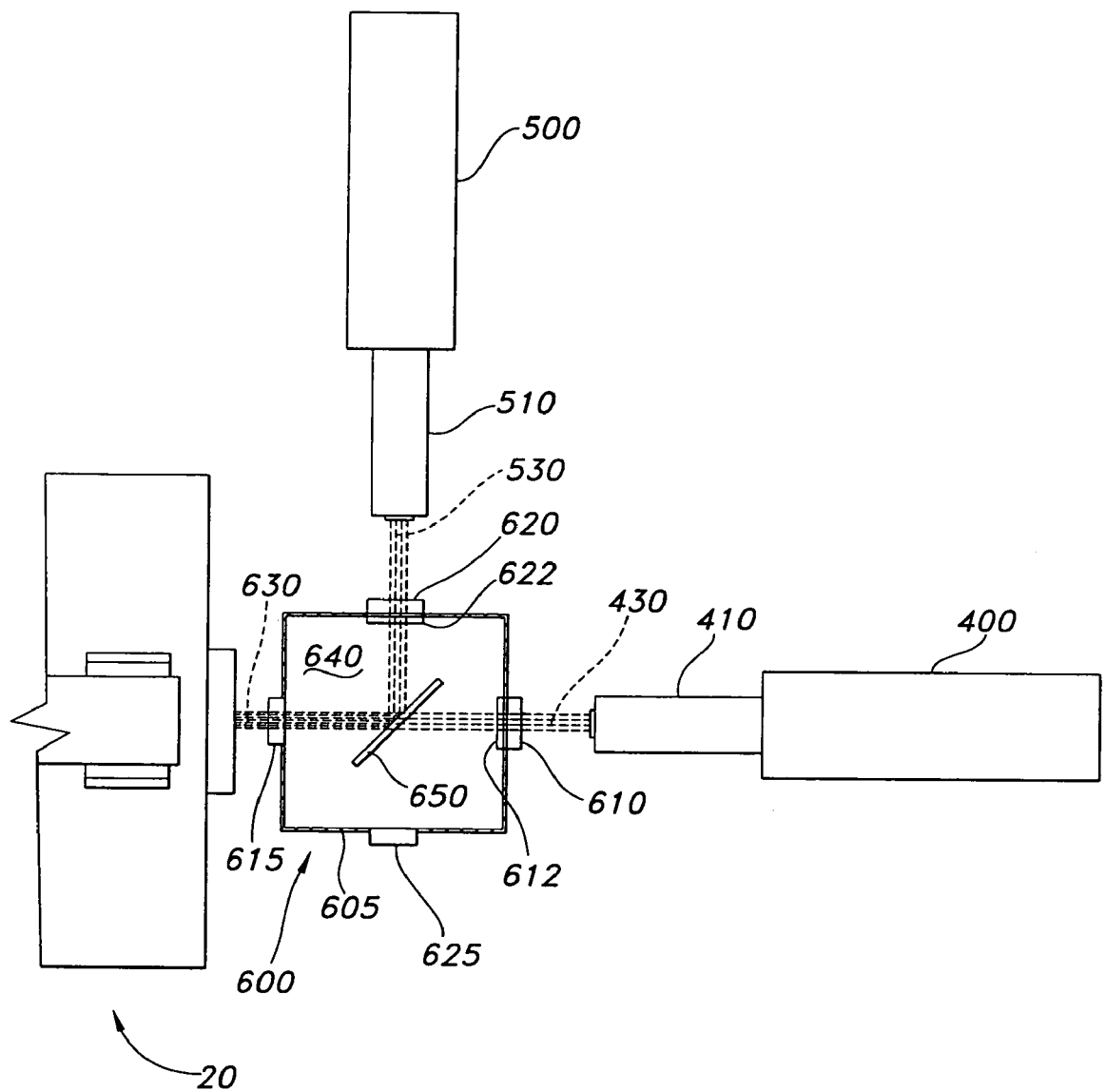
FIG. 5 is an overhead schematic view of the light waves passing through an optical combiner and entering a microscope, according to an embodiment of the present invention.

Referring to the schematic light wave diagram in FIG. 5, the first and second tunable filters 410, 510 are used to filter the light from the light sources 400, 500 and produce monochromatic (single-color, single-frequency) light waves 430, 530. The first light 430 travels at a first frequency $f_1$ and has a corresponding first wavelength $L_1$. Similarly, the second light 530 travels at a second frequency $f_2$ and has a corresponding second wavelength $L_2$. The corresponding frequencies $f_1$, $f_2$ and wavelengths $L_1$, $L_2$ may be readily calculated using Equation One (frequency equals the speed of light divided by the wavelength).

A first acousto-optic tunable filter 410 (AOTF 410) is used in the system 10 of the present invention to filter a light source 400, typically a laser beam, so that it emits a single-frequency light 430. The acousto-optic tunable filters 410, 510 may use a Tellurium Dioxide crystal and a transducer, and may be configured specifically to filter light from a laser, such as the fiber-pigtailed laser acousto-optic tunable filter, model TEAF 3-0.45-65-1FP, manufactured by Brimrose Corporation of America. It should be understood, however, that any device capable of receiving a light wave and filtering it into a single-frequency light may be used as the AOTF 410, 510.

The first AOTF 410 uses an acoustic wave to shift or change the frequency of the light waves in the laser beam from the first light source 400. The second AOTF 510 operates in a similar manner upon the second light source 500. The acoustic wave acts like a filter, interacting with the optical light waves and separating a single frequency of light from all the others. By varying the frequency of the acoustic wave, the frequency of the separated light can be varied. The frequency of the acoustic wave produced in the AOTF 410 is controlled electronically by an AOTF controller 420.

The Acousto-Optic Tunable Filter (AOTF) Controller

As shown in FIG. 4, the first AOTF controller 420 includes a first DDS driver 424 and a first RF synthesizer card 422 inside computer 50. The first DDS (Direct Digital RF Synthesizer) driver 424 may be a self-contained unit containing an RF (radio frequency) amplifier and its own power supply. The first DDS driver 424 acts as an interface between the first RF synthesizer card 422 and the first AOTF 410.

The first RF synthesizer card 422 includes a DDS module which synthesizes and sends a first radio frequency control signal 426 via the first DDS driver 424 to the first AOTF 410. The DDS module may cooperate with computer software inside the computer 50 to synthesize and send a particular first radio frequency control signal 426.

Similarly, the second AOTF controller 520 includes a second DDS driver 524 and a second RF synthesizer card 522 inside computer 50. The second DDS (Direct Digital RF Synthesizer) driver 524 may be a self-contained unit containing an RF (radio frequency) amplifier and its own power supply. The second DDS driver 524 acts as an interface between the second RF synthesizer card 522 and the second AOTF 510.

The second RF synthesizer card 522 includes a DDS module which synthesizes and sends a second radio frequency control signal 526 via the second DDS driver 524 to the second AOTF 510. The DDS module may cooperate with computer software inside the computer 50 to synthesize and send a particular second radio frequency control signal 526.

The AOTF controllers 420, 520 may be two-channel units such as the acousto-optic tunable filter controller, model VFI-145-70-DDS-A-C2-X, manufactured by Brimrose Corporation of America. It should be understood, however, that any device capable of controlling a device that receives and filters light into a single-frequency light wave may be used as the AOTF controller 420, 520.

The first and second RF control signals 426, 526 are sent by the first and second AOTF controllers 420, 520 to the first and second acousto-optic tunable filters 410, 510. The frequency of the RF control signal 426, 526 determines the frequency of the acoustic wave which is used inside each AOTF 410, 510 to filter the light emitted by each light source 400, 500 into a single-frequency light wave 430, 530.

The Optical T-Combiner

In this embodiment where two light sources 400, 500 are used, the system 10 includes an optical combiner 600 specially designed to combine the lights 430, 530 from two light sources, as shown in FIG. 5. The light sources may be any two of the following: a first light source 400, preferably a laser; a second light source 500, also preferably a laser; and an ultraviolet light source 100. The combiner 600 operates somewhat like a tee connector that might be used in other applications, so it is sometimes referred to as a T-combiner. The combiner 600 preferably includes multiple ports with SMA connectors to receive and transmit the light waves. SMA indicates a Sub-Miniature Type A fiber optic connector.

The combiner 600 of the present invention generally includes a chamber 640 enclosed within a casing 605. A quartz prism 650 inside the chamber 640 combines the two incoming light waves 430, 530. The casing 605 includes three input ports 610, 620, 625 and one output port 615 with SMA connectors. The first and second input ports 610, 620, respectively, are designed to accept input from laser light sources, and a third input port 625 is designed to accept ultraviolet light. With three input ports 610, 620, 625, the combiner 600 is capable of combining any two types of light. Alternative, the combiner 500 will transmit a single light source through the prism 650. The combiner 600 is also capable of transmitting two lights that may enter through a single port, such as those produced by a dual-channel tunable filter.

Other port configurations and prism types are contemplated and may be used in the combiner 600, according to the elements present in a particular system, provided the combiner 600 functions to combine two light waves into a single combined light wave 630 capable of provoking the combinatory phenomenon discussed herein.

Each laser input port 610, 620 includes a laser beam expander 612, 622 to focus and collimate (make parallel) the laser beam. A laser beam expander 612, 622 is designed to decrease the laser's beam spot size at large distances. The expander operates like a reverse Galilean telescope, providing a certain angular magnification factor called the expander power. The beam diameter is first increased in size by the expander power. Then, the beam divergence is reduced by the same power. This combination yields a beam that is not only larger, but also one that is highly collimated. The result is an expanded laser beam that produces a smaller beam spot at a large distance when compared to the laser alone. The expanded laser beam also produces smaller beam spot sizes when used in combination with additional focusing optics, a feature that facilitates focusing optimization.

The quartz prism 650 of the optical combiner 600 merges the light waves 430, 530 from two light sources 400, 500, resulting in a combined light wave 630 that behaves differently from any other single light source. More specifically, the combined light wave 630, after it passes through the darkfield condenser 60 and strikes the specimen 200, will produce a combinatory phenomenon.

The Combinatory Phenomenon

The two-source embodiment of the system 10 of the present invention uses the powerful effects of the combinatory phenomenon to improve the resolution D of the microscope 20. When two lights 430, 530 are combined to form a single combined light 630, the interaction of the two light waves 430, 530 traveling at frequencies $f_1$, $f_2$ produces two new combinatory frequencies; namely, a combined additive frequency Fa and a combined subtractive frequency Fs. As the terms imply, the additive frequency Fa equals $f_1+f_2$ and the subtractive frequency Fs equals $f_1-f_2$. Accordingly, the single combined light 630 includes two light waves 630A, 630S traveling at two different frequencies, Fa and Fs.

The light wave 630A traveling at the additive frequency Fa has greater energy, of course, than the light wave 630S traveling at the subtractive frequency Fs. Accordingly, the additive light wave 630A will produce the most amount of light scattering and the additive frequency Fa will determine the resolution or resolving power D of the microscope. The resolution D of the microscope 20 in the system 10 of the present invention can be calculated using Abbe's formula (D equals La divided by twice the NA), where La is the additive wavelength (corresponding to the additive frequency Fa) and NA is the numerical aperture of the darkfield condenser 60.

The resolving power D of the microscope 20 in the system 10 of the present invention is an estimate because the intensity of the Raman-scattered light 320 produced by a combined light 630 having an additive wavelength La is, to some degree, dependent upon the specimen 200 being viewed.

EXAMPLE

The interaction of two single-frequency lights 430, 530 may be illustrated by an example. A first light 430 having a first wavelength $L_1$ of $440 \times 10^{-9}$ meters is combined with a second light 530 having a second wavelength $L_2$ of $400 \times 10^{-9}$ meters. We can calculate the corresponding frequencies $f_1$, $f_2$ using Equation One (frequency equals the speed of light divided by the wavelength). The first frequency $f_1$ equals $6.81 \times 10^{14}$ Hz. The second frequency $f_2$ equals $7.49 \times 10^{14}$ Hz.

Combining light at these two frequencies $f_1$, $f_2$ produces a combined light 630 which includes light waves traveling at two different frequencies Fa, Fs. Using the frequencies $f_1$, $f_2$ calculated, the additive frequency Fa $(f_1+f_2)$ equals $14.30 \times 10^{14}$ Hz and the subtractive frequency Fs $(f_1-f_2)$ equals $0.680 \times 10^{14}$ Hz.

The light waves 630A traveling at the additive frequency Fa of $14.30 \times 10^{14}$ Hz produce light which is in the ultraviolet range of the electromagnetic spectrum. As shown in FIG. 6., generally, the higher the frequency, the higher the energy. Ultraviolet light has more energy than visible light or light in the very low frequencies such as infrared light, microwaves, and radio waves. The light waves 630S traveling at the subtractive frequency Fs of $0.680 \times 10^{14}$ Hz produce infrared light, which has a much lower energy than ultraviolet light.

The resolution D of a microscope illuminated by the combined light 630 can be calculated using Abbe's formula (D equals La divided by twice the NA). Using the light waves 630A traveling at the additive frequency Fa of $14.30 \times 10^{14}$ Hz (and its corresponding additive wavelength La of $209 \times 10^{-9}$ meters) and the numerical aperture NA of the darkfield condenser (which, in one embodiment of the system 10 is 1.41), the resolving power D of the microscope 20 is $74.1 \times 10^{-9}$ meters (741 Angstroms).

Figure 8:
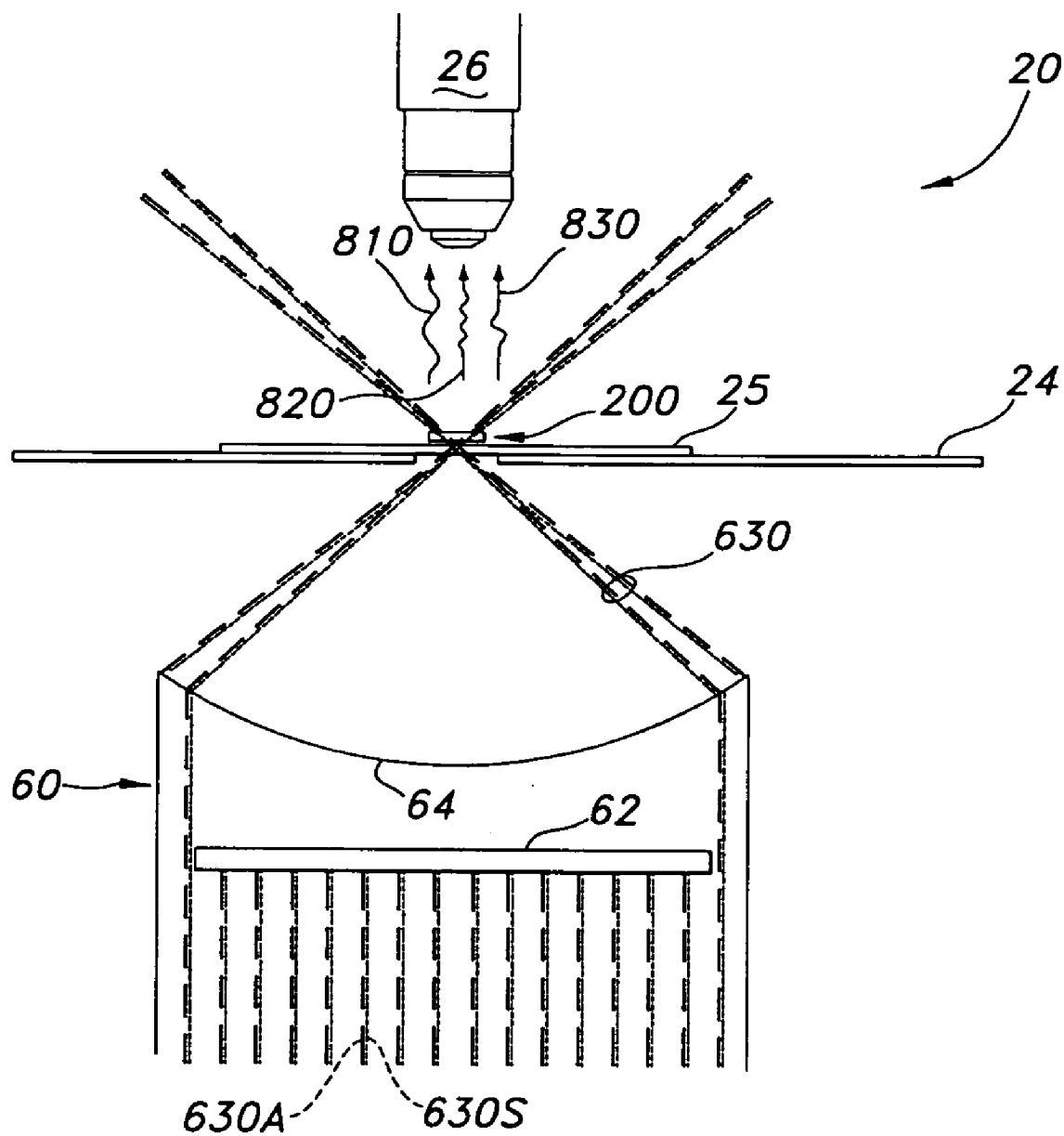
FIG. 8 is a detailed view of the combined light wave as it passes through a darkfield condenser, strikes a specimen, and enters an optical microscope, according to an embodiment of the present invention.

As shown in FIG. 8, the scattering of a light source that has undergone the combinatory phenomenon (such as the combined light wave 630) includes the scattering of both the additive light wave 630A and the subtractive light wave 630S. Accordingly, both light waves 630A, 630S will produce three types of scattered light: a same-frequency (Fa, Fs) Rayleigh component, a high-frequency (Fa+Δf, Fs+Δf) component, and a lower-frequency (Fa−Δf, Fs−Δf) component. The three scattered light components (Fs, Fs+Δf, Fs−Δf) of the subtractive light wave 630S are not shown in FIG. 8 because they possess much less energy than the additive light wave 630A.

The scattering of the additive light wave 630A, as shown in FIG. 8, includes a combined Rayleigh component 810, a high-frequency combined Raman component 820, and a low-frequency combined Raman component 830. The combined Rayleigh-scattered light 810 is emitted at the same frequency (Fa) as the additive light wave 630A. The combined high-frequency Raman-scattered light 820 is emitted at a higher frequency (Fa+Δf). The combined lower-frequency Raman-scattered light 830 is emitted at a lower frequency (Fa−Δf).

Modulating Raman-Type Scattering of a Combined Light

In the two-light embodiment, the present invention includes a method of modulating or adjusting the intensity of the combined Raman-scattered light 820 when two light waves 430, 530 are combined to produce the combinatory phenomenon. By varying the frequency of the first and second light waves 430, 530, the intensity of the combined Raman-scattered light 820 can be adjusted to achieve maximum resolving power D.

The acousto-optic tunable filters 410, 510 are used to adjust the frequency of the first and second light sources 400, 500, respectively, to achieve an increase in the intensity of the combined Raman-scattered light 820 emitted by the particular specimen 200 being viewed.

It has been observed that an increase in the intensity of the combined Raman-scattered light 820 results in an increase in resolving power D. Also, the use of increased combined light frequency Fa necessarily produces a light wave having higher energy. It has also been observed that a high-energy light source produces more of the non-linear and inelastic (Raman) effects of scattered light, which are desirable in the system 10 of the present invention.

It should be noted that the acousto-optic tunable filters 410, 510 may be adjusted to produce a wide variety of light frequencies $f_1$, $f_2$, respectively; any combination of which may be optimal for viewing a particular specimen 200. Different combinations $f_1$, $f_2$ will produce different combinatory frequencies Fa, Fs, different intensities of combined Raman-scattered light 820 and, therefore, different resolving powers D for a particular specimen 200.

It should also be noted that different combinations of light frequencies $f_1$, $f_2$ will produce different relative intensities of combined Rayleigh-scattered light 810 and combined low-energy Raman-scattered light 830, both of which may alter the effective resolving power D of the microscope system 10 for a particular specimen 200.

In another aspect of the present invention, the first and second light sources 400, 500, as shown in FIG. 4, may be of different types including, without limitation, laser, ultraviolet, x-rays, or visible light. Just as different frequency combinations $f_1$, $f_2$ will produce different relative intensities of Raman-scattered light 320, different types of light sources will produce different results.

In one configuration, the first light source 400 is a laser and the second light source 500 produces ultraviolet light. After being combined in the optical combiner 600, the combined light 630 enters the microscope 20. It is theorized that the presence of high-energy harmonics and non-linear waves from the ultraviolet light source will increase the amount and intensity of Raman-scattered light 320, thereby increasing resolution.

In another configuration, a single laser can be configured using a beam splitter to emit a laser beam into both the first and second acousto-optic tunable filters 410, 510. Each acousto-optic tunable filter 410, 510 can then filter the laser into two single-wavelength lights 430, 530.

Two Single-Frequency Light Waves from One Source

Figure 7:
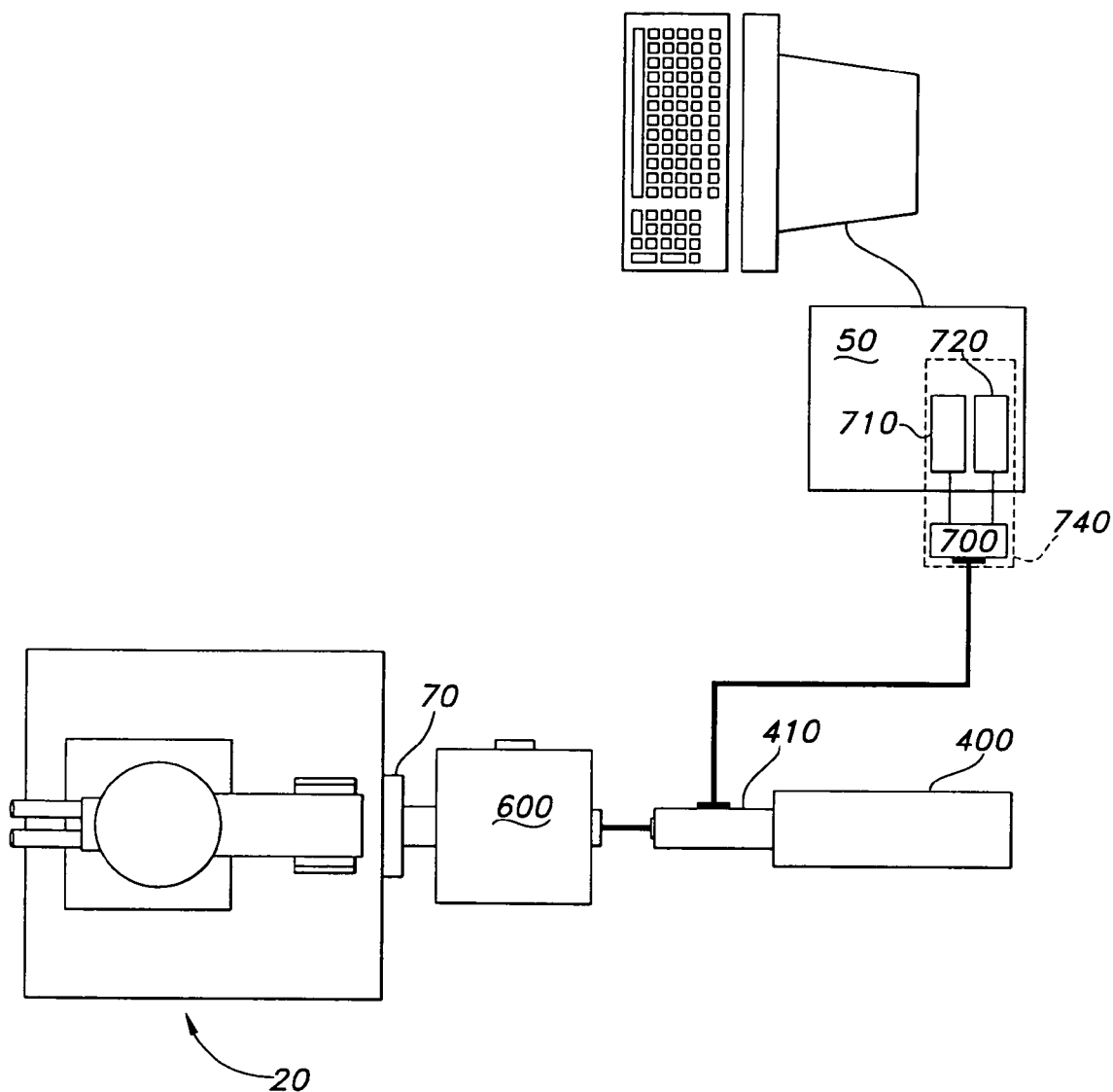
FIG. 7 is an overhead schematic view of an embodiment of the present invention that includes a dual-frequency acousto-optic filter controller.

In yet another configuration, shown in FIG. 7, a single laser source 400 can provide light waves to the acousto-optic tunable filter 410 that is controlled by a dual-frequency AOTF controller 740.

The dual-frequency AOTF controller 740 includes a dual-frequency DDS driver 700, a primary RF synthesizer card 710, and a secondary RF synthesizer card 720. The dual-frequency DDS (Direct Digital RF Synthesizer) driver 700 may be a self-contained unit containing an RF (radio frequency) amplifier and its own power supply. The dual-frequency DDS driver 700 acts as an interface between the primary and secondary RF synthesizer cards 710, 720 and the AOTF 410.

The primary RF synthesizer card 710 includes a DDS module which synthesizes and sends a primary radio frequency control signal 716 via the dual-frequency DDS driver 700 to the AOTF 410. The DDS module may cooperate with computer software inside the computer 50 to synthesize and send a particular primary radio frequency control signal 716.

Similarly, the secondary RF synthesizer card 720 includes a DDS module which synthesizes and sends a secondary radio frequency control signal 726 via the dual-frequency DDS driver 700 to the AOTF 410. The DDS module may cooperate with computer software inside the computer 50 to synthesize and send a particular secondary radio frequency control signal 726.

The dual-frequency driver 700 sends both control signals 716, 726 to the AOTF 410, which has two channels. The AOTF 410 filters the incoming light from the laser 400 into two single-frequency light waves 430, 530 and broadcasts one on each channel. In use, the dual-frequency driver 700 sends both control signals 716, 726 by alternating; in other words, by repeatedly switching from one frequency to another.

The dual-frequency driver 700, however, has a maximum switching speed. The excited states of the observed specimen 200, likewise, have certain lifetimes. Recall that the combined light 630 striking the specimen 200 causes excitation in the molecules of the specimen 200. The excited states produce the scattered light used to illuminate the specimen 200 in the microscope 20. If the lifetime of each of the excited states of the specimen 200 is longer than the maximum switching speed, then the dual-frequency driver 700 will operate successfully to produce both light waves 430, 530. For a specimen 200 having a very short excitation state, a second AOTF 410 and controller 420 may be needed. Alternatively, a dual-frequency driver 700 with a higher maximum switching speed could be used.

Experimental Results

Figures 9, 9A, 9B:
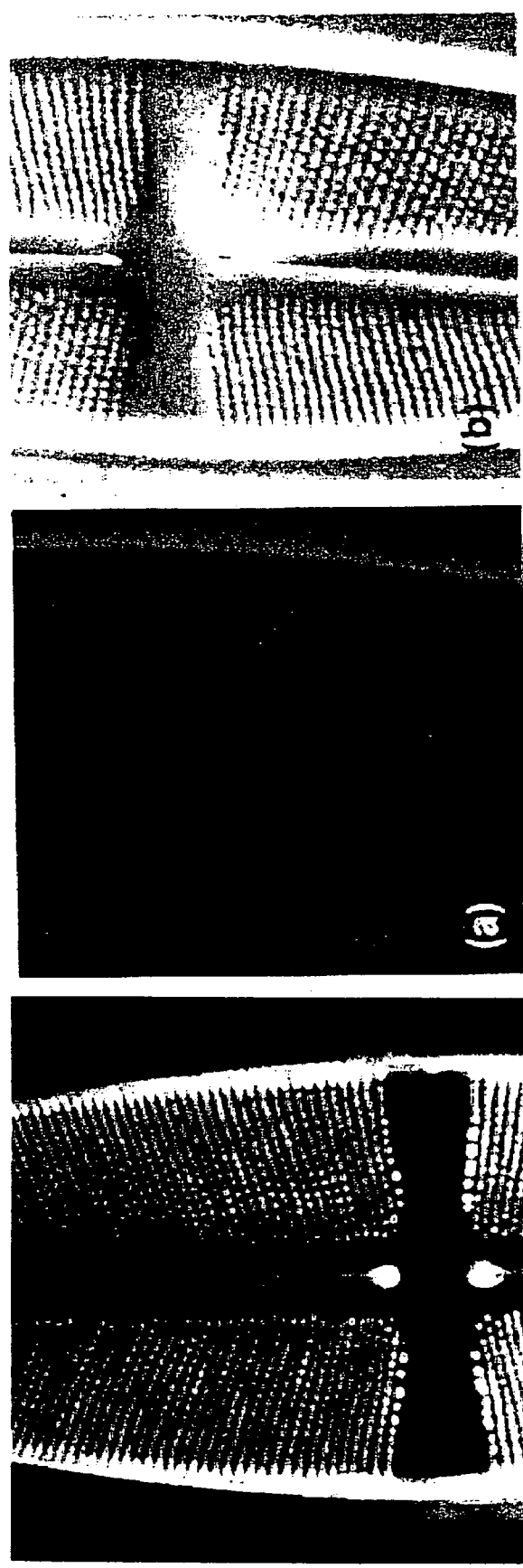
FIG. 9 is a photomicrograph of a diatom illuminated by an embodiment of the microscope system of the present invention, compared to diatom images in FIGS. 9a and 9b obtained by other microscopes.

FIG. 9 shows the intricate lattice of a diatom illuminated by an embodiment of the microscope system 10 of the present invention. A diatom is a tiny, unicellular marine organism that has a silica-impregnated outer cell wall sometimes called a lattice. Diatom lattices are often used in microscopy to study and compare systems of illumination and magnification.

The diatom lattice shown in FIG. 9 was illuminated and photographed using an embodiment of the microscope system 10 of the present invention. The system 10 used to illuminate and photograph the diatom in FIG. 9 included a 100-watt mercury lamp to produce an ultraviolet light source 100 and included a Naessens darkfield condenser 60 having a numerical aperture NA of 1.41 and a 100× objective lens 26.

Comparing the detail and texture of the diatom lattice in FIG. 9 to the images in FIGS. 9a and 9b illustrates the power of the system 10 of the present invention. FIG. 9a is a still photomicrograph taken of a video image of a similar diatom. The image in FIG. 9b was enhanced using the gain boost of a Vidicon tube camera.

Figure 12:
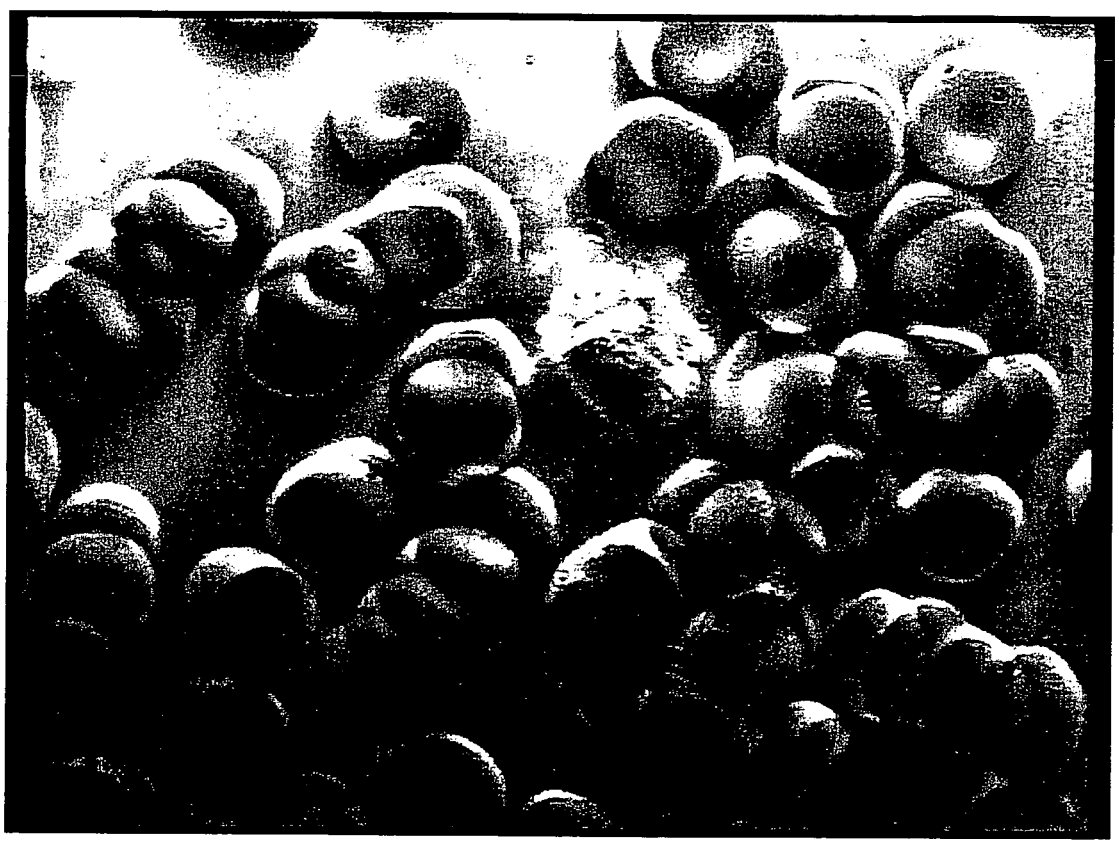
FIGS. 12 and 13 are photomicrographs of blood cells illuminated by an embodiment of the microscope system of the present invention.
Figure 13:
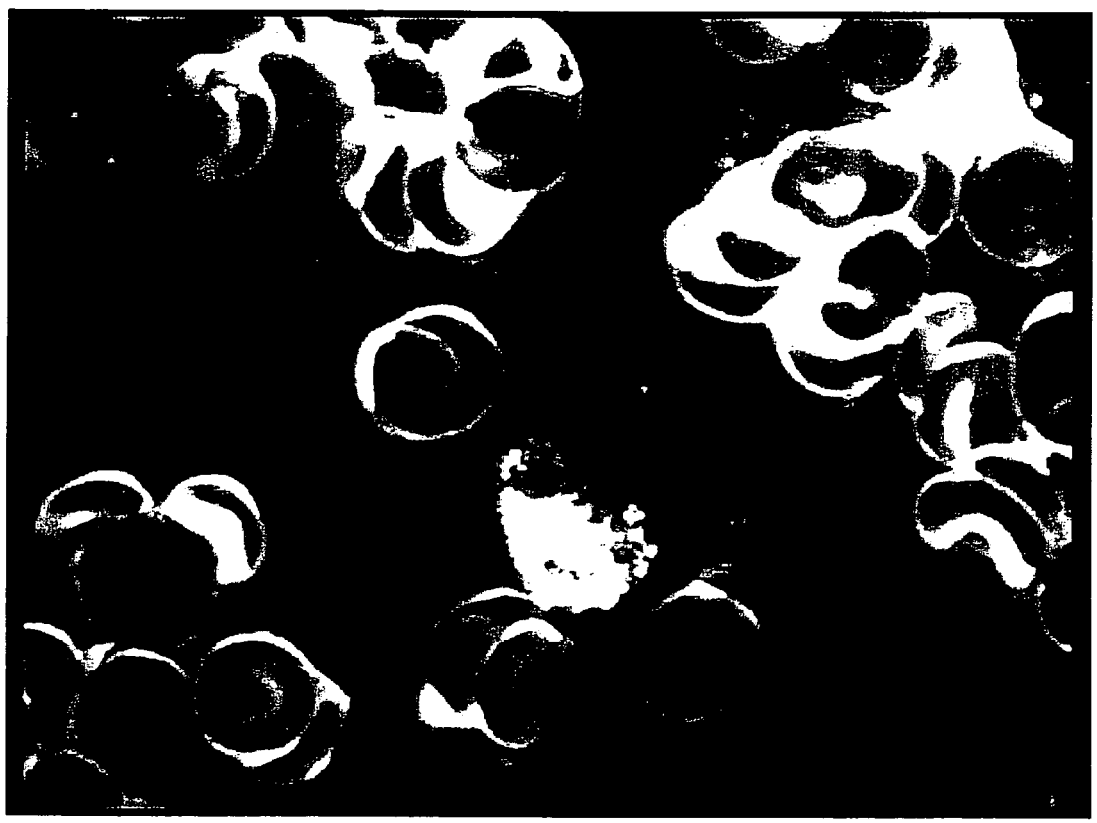

FIGS. 12 and 13 are photomicrographs of living blood cells illuminated by an embodiment of the microscope system of the present invention. Each sample was photographed approximately two minutes after the blood was drawn. Blood cells of different types, red and white, can be seen in motion, interacting with one another.

Resolution

Figure 10C:
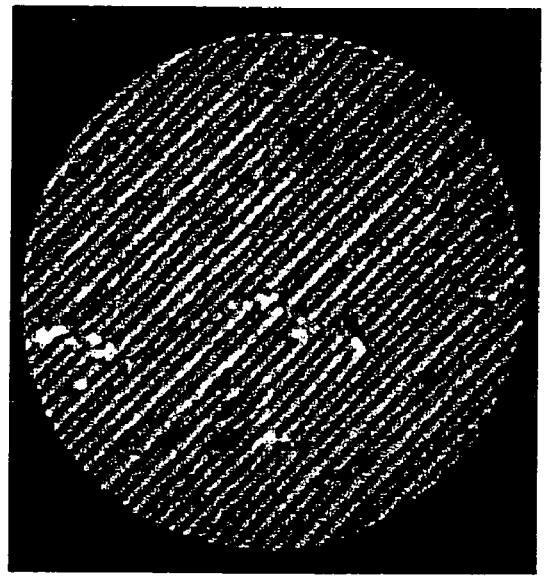
FIGS. 10a, 10b, and 10c are photomicrographs of a micrometer, an optical gage, and a carbon grating illuminated by an embodiment of the microscope system of the present invention.
Figure 10B:
Figure 10A:

Micrometers, optical gages, and carbon grating samples are used in microscopy to evaluate, calibrate, and illustrate the resolving power of microscopes. The system 10 of the present invention obtained the images in FIGS. 10a, 10b, and 10c. FIG. 10a is a photomicrograph of a micrometer with divisions 2.0 microns apart at a magnification of approximately 4,000×. FIG. 10b is a photomicrograph of an optical gage with divisions also 2.0 microns apart at a magnification of approximately 7,500×. FIG. 10c is a photomicrograph of a carbon grating sample having equidistant and parallel lines of carbon spaced 0.46 microns apart.

The microscope system 10 of the present invention may find application in numerous fields of scientific study and research including, without limitation, microbiology, bacteriology, virology, general biology, clinical hematology, industrial quality control, reproductive sciences, and any of a variety of other fields where observation of a biological specimen is desired.

The microscope system 10 of the present invention provides a direct-view of the specimen 200, instead of the indirect views offered by ultraviolet and electron microscopes. The fact that the system 10 includes a direct-view optical microscope 20 allows real-time observation with the human eye of biochemical events taking place at a microscopic, often intracellular level.

The system 10 takes full advantage of the Raman scattering phenomenon as a source of illuminating the specimen 200, providing a finer resolution and a higher magnification than is currently available from any optical microscope.

The system 10 provides a real-time image of living biological materials, including cells and intracellular structures. Very little specimen preparation is required, leaving living biological specimens unaltered and without artifacts. The system 10 allows observation of living specimens without destroying or altering their biochemical characteristics, and without killing the specimen.

The system 10 also provides a low-cost, low-expertise alternative to the more expensive and complex ultraviolet and electron microscope systems. The system 10 may also be made portable for field operation.

Although the invention has been described in terms of a preferred embodiment, it will be appreciated by those skilled in the art that additions, substitutions, modifications, and deletions not specifically described may be made without departing from the spirit and scope of the invention.

What is claimed is:

1. A method of modulating the combinatory phenomenon to illuminate and view a specimen in an optical microscope system with a combined light, said method comprising:
   filtering a first unrefined light wave to produce a first light wave traveling at a first frequency;
   filtering a second unrefined light wave to produce a second light wave traveling at a second frequency;
   combining said first and second light waves to produce said combined light wave, said combined light wave comprising an additive light wave traveling at an additive frequency and a subtractive light wave traveling at a subtractive frequency;
   condensing said combined light wave into the shape of a hollow cone; and
   focusing the first vertex of said hollow cone of combined light upon said specimen.

2. The method of claim 1, wherein said specimen is placed upon a slide and is covered by a cover glass, said method further comprising:

placing a lower oil drop on the underside center of said slide;

positioning said slide on the center of said darkfield condenser;

placing an upper oil drop on the top center of said cover glass;

raising said darkfield condenser until said upper oil drop contacts said objective lens.

3. The method of claim 1, wherein the first and second unrefined light waves are of the same type in the electromagnetic spectrum.

4. The method of claim 1, wherein the first unrefined light wave is of a type different than the second unrefined light wave in the electromagnetic spectrum.

5. The method of claim 1, wherein the first unrefined light wave comprises a light wave from a laser and the second unrefined light wave comprises a light wave form a non-laser source.

6. The method of claim 1, wherein the step of filtering the first unrefined light wave further comprises filtering with an acousto-optic tunable filter.

7. The method of claim 1, wherein the step of combining the first and second light waves to produce the combined light wave includes combining the light waves with an optical combiner having a prism assembly for reflecting the combined light through an output port of the optical combiner.

\* \* \* \* \*